United States Patent
Udayampalayam Palanisamy et al.

(10) Patent No.: US 8,431,562 B2
(45) Date of Patent: Apr. 30, 2013

(54) CRYSTALLINE SODIUM SALT OF CEPHALOSPORIN ANTIBIOTIC

(75) Inventors: Senthilkumar Udayampalayam Palanisamy, Chennai (IN); Sivakumar Balasubramanian, Chennai (IN); Manimaran Arasappan, Chennai (IN); Meenakshi Sundaram Soma Sundaram, Chennai (IN); Sureshkumar Kanagaraj, Chennai (IN); Mohan Singaravel, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 187 days.

(21) Appl. No.: 13/054,262

(22) PCT Filed: Aug. 20, 2009

(86) PCT No.: PCT/IB2009/006609
§ 371 (c)(1),
(2), (4) Date: Feb. 8, 2011

(87) PCT Pub. No.: WO2010/020871
PCT Pub. Date: Feb. 25, 2010

(65) Prior Publication Data
US 2011/0136777 A1 Jun. 9, 2011

(30) Foreign Application Priority Data
Aug. 22, 2008 (IN) .............. 2047/CHE/2008

(51) Int. Cl.
*C07D 501/36* (2006.01)
*A61K 31/546* (2006.01)

(52) U.S. Cl.
USPC .................... 514/206; 540/227

(58) Field of Classification Search .......... None
See application file for complete search history.

(56) References Cited

U.S. PATENT DOCUMENTS

| | | | |
|---|---|---|---|
| 4,464,367 A | 8/1984 | Labeeuw et al. | |
| 4,902,683 A | 2/1990 | Amin et al. | |
| 4,937,330 A | 6/1990 | Sacks et al. | |
| 5,013,713 A | 5/1991 | Mitchell | |
| 5,079,007 A | 1/1992 | Putnam | |
| 5,721,359 A | 2/1998 | Dunn et al. | |
| 6,458,949 B1 * | 10/2002 | Handa et al. | 540/226 |
| 6,555,680 B1 * | 4/2003 | Deshpande et al. | 540/227 |
| 6,610,845 B1 * | 8/2003 | Deshpande et al. | 540/215 |
| 6,803,461 B2 * | 10/2004 | Deshpande et al. | 540/226 |
| 7,071,329 B2 * | 7/2006 | Monguzzi et al. | 540/226 |
| 7,345,169 B2 * | 3/2008 | Senthilkumar et al. | 544/227 |
| 7,511,135 B2 * | 3/2009 | Tyagi et al. | 540/227 |
| 8,212,024 B2 * | 7/2012 | Senthilkumar et al. | 540/227 |
| 2002/0082248 A1 * | 6/2002 | Berger et al. | 514/206 |
| 2004/0132996 A1 * | 7/2004 | Tyagi et al. | 540/227 |
| 2005/0119244 A1 * | 6/2005 | Monguzzi et al. | 514/202 |
| 2006/0094872 A1 * | 5/2006 | Senthilkumar et al. | 540/217 |
| 2006/0135761 A1 * | 6/2006 | Datta et al. | 540/222 |
| 2008/0207912 A1 * | 8/2008 | Tyagi et al. | 548/195 |
| 2011/0059933 A1 * | 3/2011 | Kanagaraj et al. | 540/227 |

FOREIGN PATENT DOCUMENTS

| | | |
|---|---|---|
| IN | 2003MU01140 | * 10/2003 |
| IN | 2005CH01773 | * 12/2005 |
| WO | WO 2007/042917 AI | 4/2007 |

OTHER PUBLICATIONS

Indian Patent Application No. 2023/CHE/2007 filed Sep. 10, 2007 in the name of Senthilkumar Udayampalayam Palanisamy.
International Search Report for International Patent Application No. PCT/IB2009/006609, mailed on Feb. 19, 2010.

* cited by examiner

*Primary Examiner* — Mark Berch
(74) *Attorney, Agent, or Firm* — Oliff & Berridge, PLC

(57) ABSTRACT

Polymorphs of Ceftiofur sodium as a crystalline product and a process for the preparation of polymorphs of crystalline Ceftiofur sodium of formula (I).

16 Claims, 6 Drawing Sheets

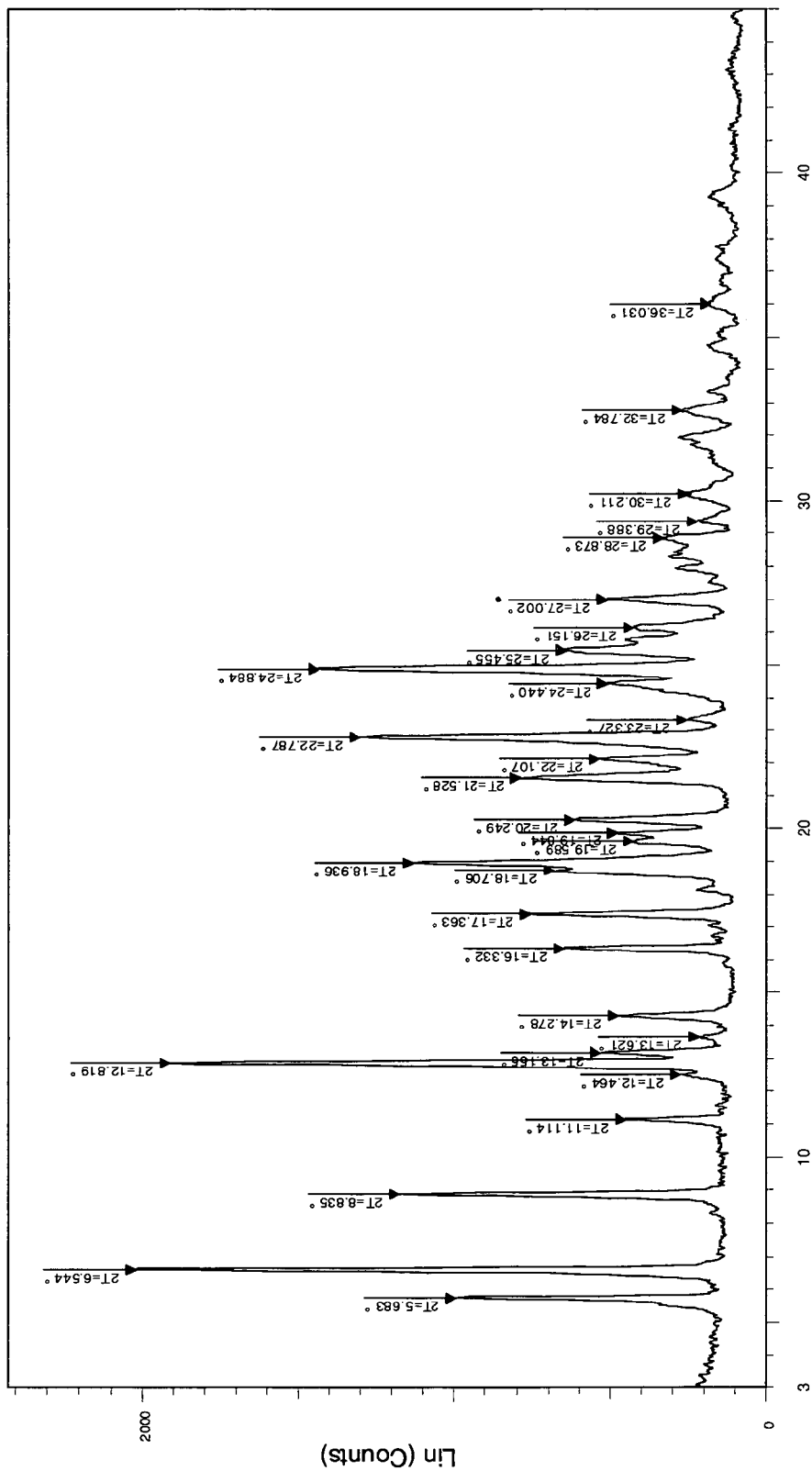
FIG.1. PXRD OF CRYSTALLINE ANHYDROUS CEFTIOFUR SODIUM (FORM-A)

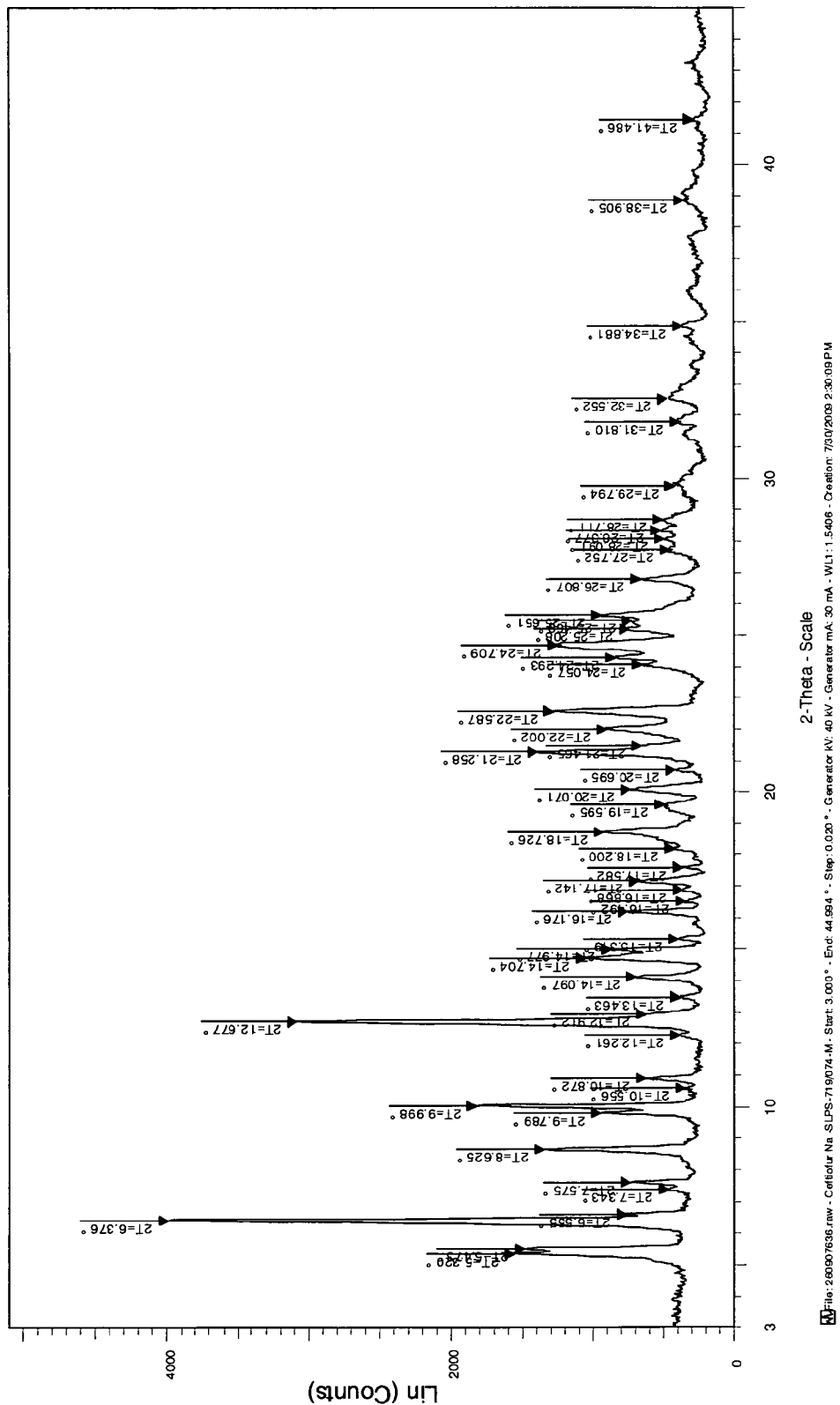
FIG.2. PXRD OF CRYSTALLINE CEFTIOFUR SODIUM (FORM-M)

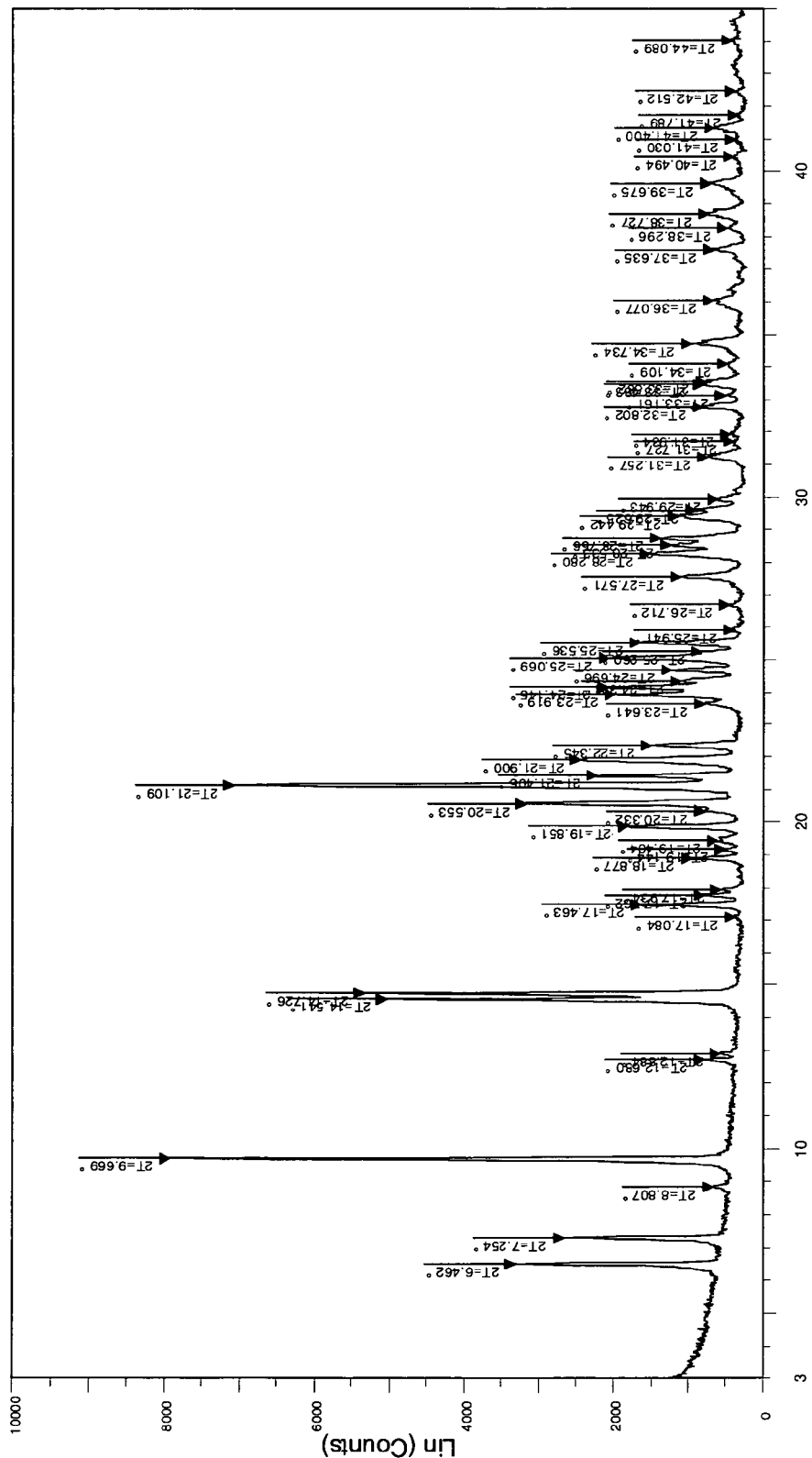
FIG. 3. PXRD OF CRYSTALLINE CEFTIOFUR SODIUM (FORM-D)

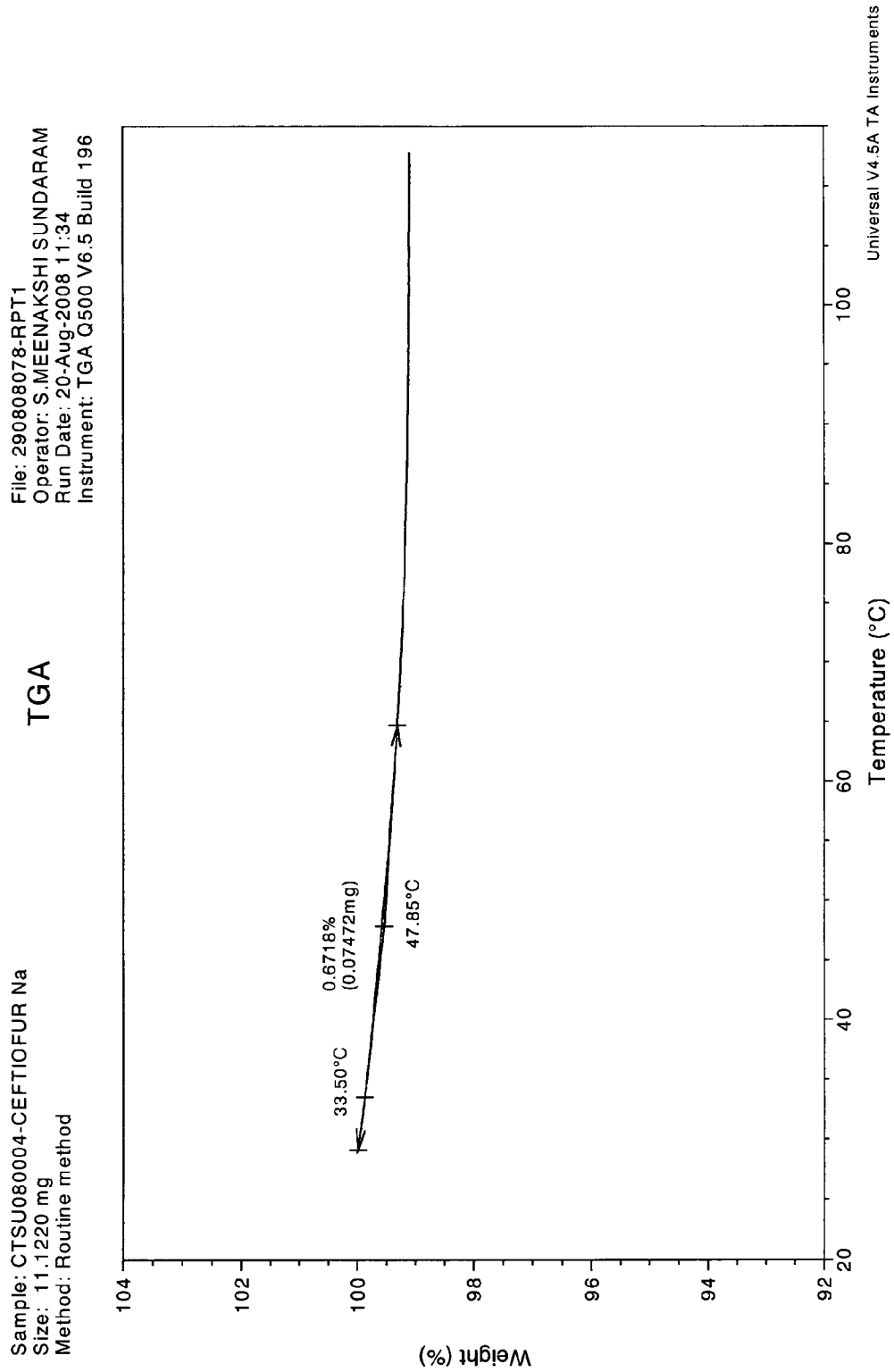
FIG. 4. TGA CURVE OF CRYSTALLINE ANHYDROUS CEFTIOFUR SODIUM (FORM-A)

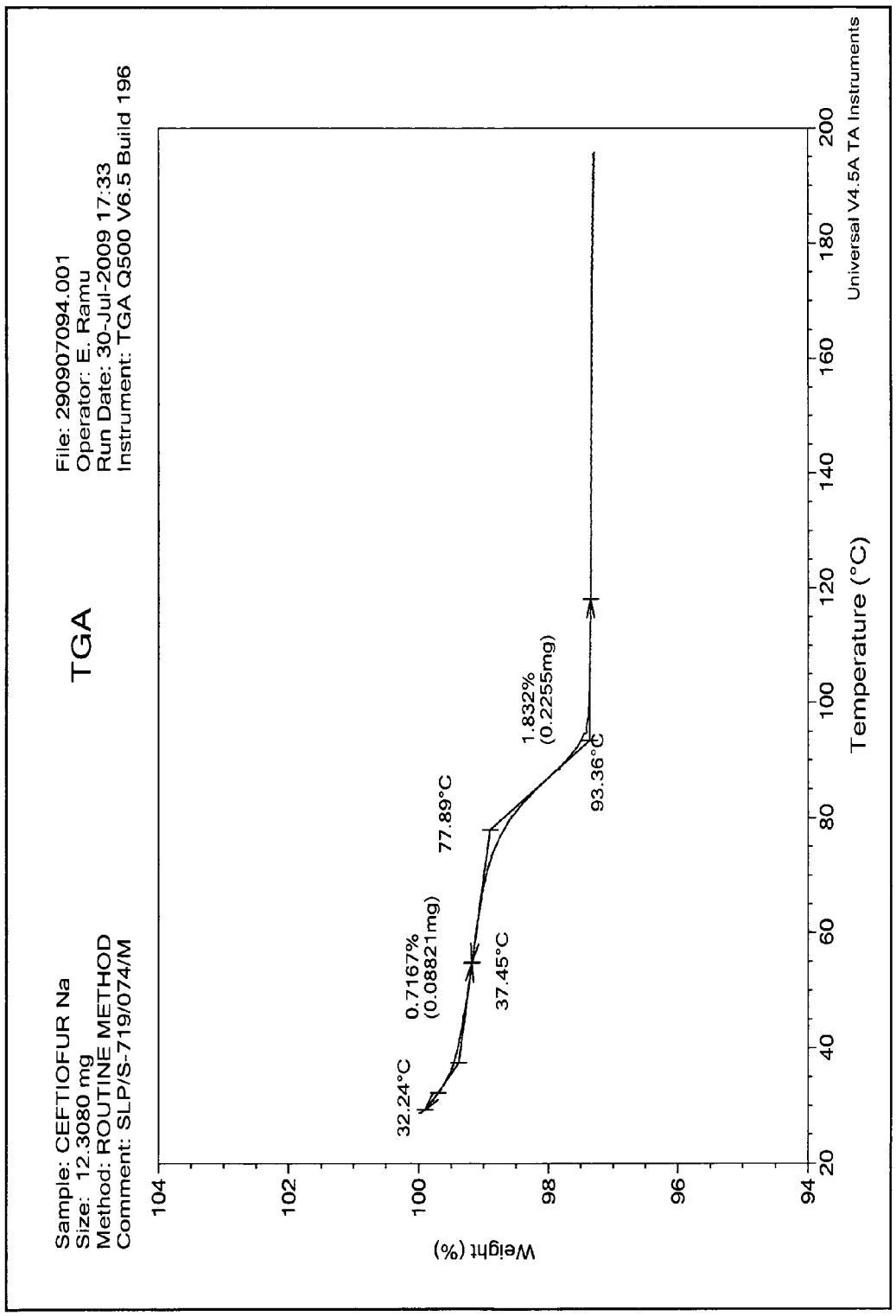
FIG.5. TGA CURVE OF CRYSTALLINE CEFTIOFUR SODIUM (FORM-M)

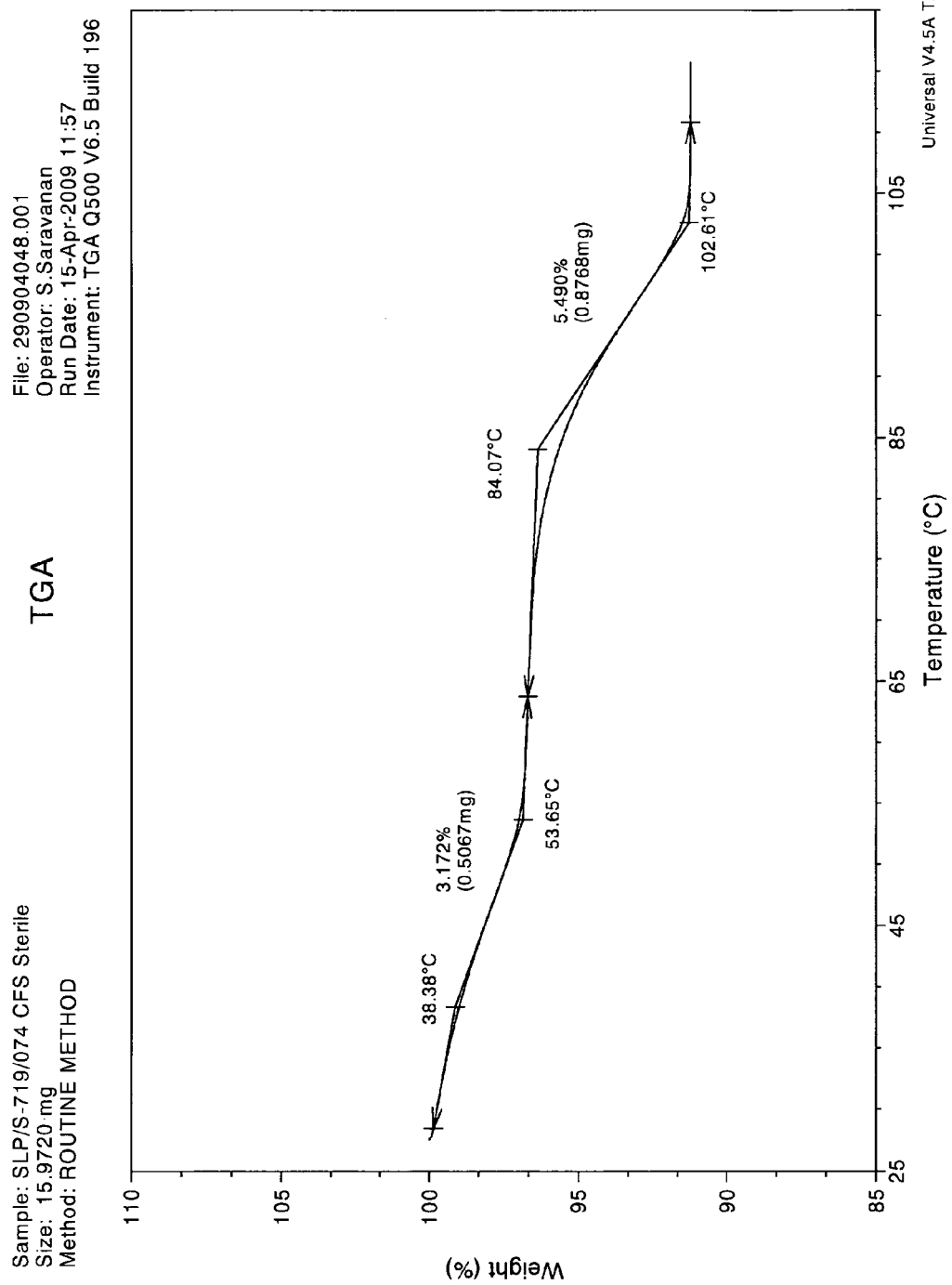
FIG.6. TGA CURVE OF CRYSTALLINE CEFTIOFUR SODIUM (FORM-D)

CRYSTALLINE SODIUM SALT OF CEPHALOSPORIN ANTIBIOTIC

FIELD OF THE INVENTION

The present invention relates to novel polymorphs of Ceftiofur sodium as a crystalline product. This invention further relates to a process for the preparation of novel polymorphs of Ceftiofur sodium.

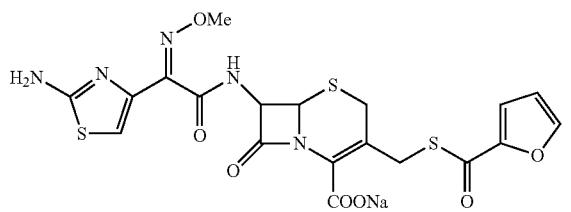

BACKGROUND OF THE INVENTION

Ceftiofur, a semisynthetic cephalosporin, is a broad-spectrum antibiotic against both Gram-positive and Gram-negative bacteria including beta-lactamase-producing bacterial strains and anaerobes. Its antibacterial activity results from the inhibition of mucopeptide synthesis in the cell wall in a similar fashion to other cephalosporins. Ceftiofur is used in the treatment of respiratory infections in cattle and pigs. The chemical designation is 7-[[(2-amino-4-thiazolyl)(methoxyimino)acetyl]amino]-3-[[2-furanylcarbonyl)thio]methyl]-8-oxo-5-thia-1-azabicyclo[4.2.0]oct-2-ene-2-carboxylic acid. The sodium and hydrochloride salts are administered intramuscularly and intravenously.

Ceftiofur is first disclosed in U.S. Pat. No. 4,464,367, which also discloses a process for preparing Ceftiofur and its sodium salt.

U.S. Pat. No. 4,902,683 claims crystalline hydrochloride salt of Ceftiofur. According to this patent the conventional free acid and its sodium salt are unstable and are obtained as amorphous in nature.

U.S. Pat. No. 5,721,359 claims crystalline Ceftiofur free acid and process for the preparation of same.

U.S. Pat. No. 4,937,330 claims a process for the preparation of Ceftiofur sodium. Though this patent mentioned the Ceftiofur sodium obtained as crystal form, this patent does not provide the X-ray diffraction pattern of the said crystal. According to this patent Ceftiofur sodium is isolated from aqueous tetrahydrofuran as a unique solid phase characterized by birefringent lath- and rod-shaped particles. Moreover further treatment with a dry, organic solvent (e.g., acetone or ethanol) produces solvent-free amorphous Ceftiofur sodium upon drying.

Hence all the prior art literature reported so far provide amorphous Ceftiofur sodium, and owing to the amorphous nature, the conventional Ceftiofur sodium is less stable. Further, owing to the amorphous nature, purification is very difficult, and hence not preferable in large scale preparation.

In our PCT publication WO 2007/042917 (Indian Application No. 1462/CHE/2005) a novel polymorph of crystalline Ceftiofur Sodium having moisture content in the range of 7.0 to 11.0% is provided and is named as Form D.

In our continued research we have identified novel anhydrous crystalline form of Ceftiofur sodium, which is having good stability over conventional amorphous product. None of the prior art suggests or even motivates the present invention.

OBJECTIVES OF THE INVENTION

The primary objective of the present invention is to provide an anhydrous crystalline polymorph of Ceftiofur sodium of formula (I) hereinafter called as Form A of Ceftiofur sodium, which is having good stability than conventional amorphous Ceftiofur sodium.

Another objective of the present invention is to provide a crystalline polymorph of Ceftiofur sodium of formula (I) having moisture content in the range of 3.0-4.5% hereinafter called as Form M of Ceftiofur sodium.

Yet another objective of the present invention is to provide a pharmaceutical composition containing crystalline polymorph of Form A or Form M or mixture of both the forms of Ceftiofur sodium.

Still another objective of the invention is to provide a process for the preparation of crystalline polymorph of Form A and Form M of Ceftiofur sodium.

SUMMARY OF THE INVENTION

Accordingly, the present invention provides novel anhydrous crystalline polymorph of Ceftiofur sodium (Form A) of formula (I)

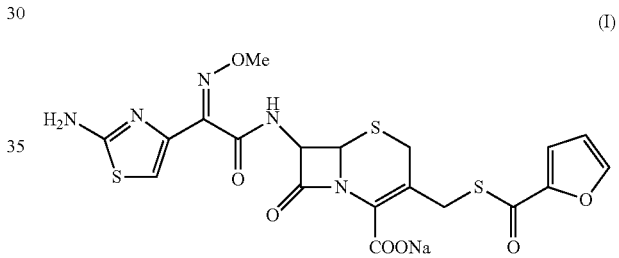

having substantially the same X-ray diffractogram as set out in FIG. 1.

The present invention also provides a process for the preparation of novel anhydrous crystalline polymorph of Ceftiofur sodium (Form A) of formula (I), which comprises drying the hydrated Ceftiofur sodium (Form D) at a temperature in the range of 60° C. to 125° C., till the moisture content reaches 0.4 to 2.0%.

The present invention further provides a novel crystalline polymorph of Ceftiofur sodium (Form M) of formula (I), having moisture content in the range of 3.0-4.5% which is substantially the same X-ray diffractogram as set out in FIG. 2.

The present invention also provides a process for the preparation of novel crystalline polymorph of Ceftiofur sodium (Form M) of formula (I) having moisture content 3.0-4.5%, which comprises controlled drying of hydrated polymorph of Ceftiofur sodium (Form D) at 70° C. under vacuum till the moisture content reaches 3.0 to 4.5%.

DESCRIPTION OF FIGURES

FIG. 1: Powder XRD pattern of novel anhydrous crystalline form of Ceftiofur sodium of formula (I) (Form A);

FIG. 2: Powder XRD pattern of novel crystalline form of Ceftiofur sodium of formula (I) having moisture content 3.0-4.5% (Form M); and FIG. 3: Powder XRD pattern of hydrated crystalline form of Ceftiofur sodium of formula (I) having moisture content 7.0-11.0% (Form D); analyzed by X-Ray Powder Diffractometer of following features:

| | |
|---|---|
| Make | BRUKER AXS |
| Model | D8 ADVANCE |
| Data handling system | EVA 12.0.0.0. |
| ANODE | COPPER |
| RADIATION | COPPER K alpha-1 |
| WAVELENGTH | 1.5406 A° |
| CURRENT &VOLTAGE | 40 kV 30 mA |

FIG. 4: Thermo Gravimetric Analysis (TGA) pattern of novel anhydrous crystalline form of Ceftiofur sodium of formula (I) (Form A);

FIG. 5: Thermo Gravimetric Analysis (TGA) pattern of novel crystalline form of Ceftiofur sodium of formula (I) having moisture content 3.0-4.5% (Form M); and FIG. 6: Thermo Gravimetric Analysis (TGA) pattern of hydrated crystalline form of Ceftiofur sodium of formula (I) having moisture content 7.0-11.0% (Form D); analyzed by Universal V4.2E TA Instruments of following features:

| | |
|---|---|
| Make | TA Instruments |
| Model | TGA Q500 |
| Data handling software | Universal Analysis 2000 |
| Purge gas | Nitrogen [Sample flow rate: 60 ml/min, Balance flow rate: 40 ml/min] |
| Ramp | 10° c./min |

DETAILED DESCRIPTION OF THE INVENTION

In an embodiment of the present invention, novel anhydrous crystalline polymorph of Ceftiofur sodium (Form A) of formula (I) is characterized by X-ray powder diffraction peaks as shown in the following table:

| 2-Theta | I % |
|---|---|
| 5.68 | 49.2 |
| 6.54 | 100.0 |
| 8.84 | 58.1 |
| 11.11 | 22.1 |
| 12.46 | 13.3 |
| 12.82 | 94.6 |
| 13.16 | 26.0 |
| 13.62 | 10.4 |
| 14.28 | 23.3 |
| 16.33 | 32.0 |
| 17.36 | 37.3 |
| 18.71 | 33.6 |
| 18.94 | 55.9 |
| 19.59 | 20.9 |
| 19.84 | 23.3 |
| 20.25 | 30.4 |
| 21.53 | 38.9 |
| 22.11 | 26.3 |
| 22.79 | 64.5 |
| 23.33 | 12.4 |
| 24.44 | 25.0 |
| 24.88 | 71.1 |
| 25.46 | 31.6 |
| 26.15 | 20.9 |
| 27.00 | 25.0 |
| 28.87 | 16.2 |
| 29.39 | 10.7 |
| 30.21 | 12.1 |
| 32.78 | 13.2 |
| 36.03 | 8.7 |

In another embodiment of the present invention, novel crystalline polymorph of Ceftiofur sodium (Form M) of formula (I) having moisture content 3.0-4.5% is characterized by X-ray powder diffraction peaks as shown in the following table:

| 2-Theta | I % |
|---|---|
| 5.32 | 38.9 |
| 5.47 | 37.1 |
| 6.38 | 100.0 |
| 6.56 | 18.9 |
| 7.34 | 11.4 |
| 7.58 | 18.2 |
| 8.63 | 33.5 |
| 9.79 | 23.5 |
| 9.99 | 45.4 |
| 10.56 | 8.4 |
| 10.87 | 15.5 |
| 12.26 | 9.4 |
| 12.68 | 77.3 |
| 12.91 | 15.4 |
| 13.46 | 9.3 |
| 14.10 | 17.3 |
| 14.70 | 26.3 |
| 14.98 | 21.6 |
| 15.32 | 9.7 |
| 16.18 | 18.7 |
| 16.49 | 8.4 |
| 16.87 | 8.9 |
| 17.14 | 16.7 |
| 17.58 | 9.0 |
| 18.20 | 10.4 |
| 18.73 | 23.0 |
| 19.60 | 12.1 |
| 20.07 | 18.2 |
| 20.70 | 10.2 |
| 21.26 | 34.8 |
| 21.47 | 16.3 |
| 22.00 | 22.5 |
| 22.59 | 31.8 |
| 24.06 | 16.1 |
| 24.29 | 20.9 |
| 24.71 | 31.2 |
| 25.21 | 18.5 |
| 25.47 | 18.0 |
| 25.65 | 23.4 |
| 26.81 | 16.4 |
| 27.75 | 11.2 |
| 28.09 | 12.3 |
| 28.38 | 12.9 |
| 28.71 | 12.5 |
| 29.79 | 10.3 |
| 31.81 | 9.4 |
| 32.55 | 11.6 |
| 34.88 | 9.0 |
| 38.91 | 8.6 |
| 41.49 | 6.8 |

In still another embodiment of the present invention, novel anhydrous crystalline polymorph of Ceftiofur sodium (Form A) of formula (I) having the following X-ray diffraction characteristic peaks (±0.2°2θ): 5.68, 6.54, 8.84, 12.82, 13.16, 16.33, 17.36, 18.71, 18.94, 20.25, 21.53, 22.11, 22.79, 24.44, 24.88, 25.46, and 27.00 in °2θ. The anhydrous crystalline Ceftiofur sodium of the present invention has moisture content in the range of 0.4 to 2.0%. The anhydrous Ceftiofur sodium (Form A) is prepared by drying the Ceftiofur sodium either under vacuum or under normal pressure at a temperature in the range of 60-125° C. till the moisture content reaches 0.4 to 2.0%. The moisture content of Ceftiofur sodium is measured by using Karl-Fisher technique.

In yet another embodiment of the present invention, novel crystalline polymorph of Ceftiofur sodium (Form M) of formula (I) having moisture content in the range of 3.0-4.5% is characterized by the following X-ray diffraction peaks (±0.2°2θ): 5.32, 5.47, 6.38, 8.63, 9.79, 9.99, 12.68, 14.70, 14.98, 18.73, 21.26, 22.00, 22.59, 24.29, 24.71 and 25.65 in °2θ.

In one more embodiment of the present invention, the crystalline polymorph of Ceftiofur sodium (Form M) of formula (I) having moisture content 3.0-4.5% is obtained by controlled drying of hydrated Ceftiofur sodium (Form D) under vacuum at 70° C. for 6-8 hours till the moisture content reaches 3.0 to 4.5%. The moisture content of Ceftiofur sodium is measured by using Karl-Fisher technique.

The starting material of the present invention can be prepared or obtained by utilizing the process available in the prior art (for example prepared by utilizing the technique available in WO 2007/042917).

Crystalline materials are preferred in most pharmaceutical applications since crystalline forms have better flow properties, and are thermodynamically more stable than amorphous forms of the same substance. This thermodynamic stability is reflected in the lower solubility and improved physical stability of the crystalline form. The regular packing of the molecules in the crystalline solid denies the incorporation of chemical impurities. Hence crystalline materials generally possess higher chemical purity than their amorphous counterparts. Further anhydrous materials are easy to handle during pharmaceutical dosage preparation.

In one more embodiment of the present invention, the Ceftiofur sodium obtained according to the present invention having good stability over conventional amorphous Ceftiofur sodium and also has less residual solvent over the amorphous sample prepared by prior art.

The following table provides a comparison of physical characteristics of amorphous and anhydrous crystalline Ceftiofur Sodium (Form A). From this table, it is evident that the anhydrous crystalline Ceftiofur Sodium has better physical characteristics than amorphous material.

TABLE 1

Comparison between Amorphous and Anhydrous Crystalline Ceftiofur sodium (Form A)

| No | Test | Amorphous | Anhydrous Crystalline (Form A) |
|---|---|---|---|
| 1 | Description | Pale yellow to pale brown powder | Almost white to white sample |
| 2 | Tapped Bulk density | 0.5 g/ml | 0.7 g/ml |
| 3 | Reconstituted solution color | Pale Brown | Colorless to pale yellow |
| 4 | Total Related substances | 1.55% | 0.15% |
| 5 | Nature | Hygroscopic in nature | Non-Hygroscopic |

The following tables (Table 2 & 3) provide stability data of anhydrous crystalline Ceftiofur Sodium (Form A) prepared according to this invention. From this table it is evident that the anhydrous crystalline Ceftiofur Sodium prepared according this invention is very stable and highly pure, which is clearly indicated by total RS (Related substances) analysis & the stability data.

TABLE 2

| Stability at 40 ± 2° C. & 75 ± 5% RH | | | | | | | | |
|---|---|---|---|---|---|---|---|---|
| Assay | | | Total RS | | | Moisture Content | | |
| Int. | 3 M | 6 M | Int. | 3 M | 6 M | Int. | 3 M | 6 M |
| 99.74 | 98.14 | 98.64 | 0.15 | 0.19 | 0.33 | 1.05 | 1.08 | 1.54 |

Int: Initial,
3 M: 3 Months;
6 M: 6 month

TABLE 3

| Stability at 25 ± 2° C. & 60 ± 5% RH | | | | | | | | |
|---|---|---|---|---|---|---|---|---|
| Assay | | | Total RS | | | Moisture Content | | |
| Int. | 3 M | 6 M | Int. | 3 M | 6 M | Int. | 3 M | 6 M |
| 99.74 | 98.84 | 99.47 | 0.15 | 0.16 | 0.21 | 1.05 | 1.05 | 1.11 |

Int: Initial,
3 M: 3 Months;
6 M: 6 month

Because of the good stability and purity of anhydrous crystalline Ceftiofur sodium as indicated by the above said tables, the potency of anhydrous crystalline Ceftiofur sodium is maintained over a long shelf life period unlike the amorphous Ceftiofur Sodium.

Form A and Form M of Ceftiofur sodium obtained according to the present invention may be used for the same indications as Ceftiofur sodium provided by a prior art process or Ceftiofur sodium currently on the market. Form A and Form M of Ceftiofur sodium according to this invention useful as the active antibiotic drug compound in pharmaceutical dosage forms for treating valuable mammalian animals and humans to treat bacterial infections in that valuable animal or human, and more particularly useful as a veterinary antibiotic drug to treat valuable animals such as cattle, swine, horses, sheep, goats, dogs and cats to fight the effects of bacterial infections caused by susceptible organisms, such as *Pasturella hemolitica, Pasturella multiocida, Salmonella typhimurium, Salmonella choleraeasuis, Actinbacillus plearopneumoniae, Streptococcus suis, Haemophilus somnus, E. coli, Staphylococcus aureus* and the like, some of which are commonly associated with diseases in animals, such as bovine respiratory disease and swine respiratory disease.

In one more embodiment of the present invention the Form A and Form M of Ceftiofur sodium prepared according to the present invention may be administered in any conventional dosage form in any conventional manner, routes of administration and dosage form are exemplified in various prior art related to Ceftiofur and also exemplified in U.S. Pat. No. 4,464,367; U.S. Pat. No. 4,902,683, U.S. Pat. No. 5,079,007, U.S. Pat. No. 5,013,713, and U.S. Pat. No. 5,721,359.

Apart from the conventional formulation that are described for the Ceftiofur sodium, formulation may also contain chelating agent like ethylene diamine tetraacetic acid (EDTA) or a buffer like sodium citrate along with or with out conventional excipient. The pharmaceutical composition may also contain amorphous Ceftiofur sodium along with crystalline Ceftiofur sodium. Surprisingly, it has been observed that the anhydrous crystalline Ceftiofur sodium as well as mixture of anhydrous crystalline and amorphous Ceftiofur sodium are non-hygroscopic in nature, whereas conventional amorphous Ceftiofur sodium is highly hygroscopic in nature. Because of the hygroscopic nature, amorphous form is relatively less stable and handling the hydroscopic material is difficult especially in large scale preparation. Due to the non-hygroscopic in nature, the stability of Form A of Ceftiofur sodium is found to be good due to which the potency is maintained for the longer shelf life period, whereas in the case of amorphous product the potency is decreasing over the shelf life period since amorphous Ceftiofur sodium is less stable.

Many other beneficial results can be obtained by applying the disclosed invention in a different manner or by modifying the invention with the scope of disclosure.

The present invention is provided by the examples below, which are provided by way of illustration only and should not be considered to limit the scope of the invention.

EXAMPLE 1

Preparation of Anhydrous Crystalline Ceftiofur Sodium (Form A)

Method A:
The crystalline Ceftiofur sodium having moisture content about 9.0% (prepared according to the process provided in WO 2007/042917) was heated to 115° C. in oven to yield anhydrous crystalline Ceftiofur sodium of the present invention.
Purity: 99.50%. Moisture content: 0.5%.
Method B:
To a clear solution of Ceftiofur sodium (200 g) in water (2500 ml) were added a solution of sodium bicarbonate in water to adjust the pH to 7.0-8.0 followed by a solution of sodium chloride (200 g) in water (800 ml) at 25-35° C. slowly. The resultant suspension was stirred for 60-120 minutes at 10-30° C. The solid obtained was filtered, washed with water and dried under vacuum at 60-70° C. till to get moisture content <1% to yield anhydrous crystalline Ceftiofur sodium in pure form. Yield: 155 g, Moisture content: 0.66%, HPLC purity: 99.95%.

The sample obtained by the above methods having the powder XRD pattern substantially same as depicted in FIG. 1 and having TGA curve substantially same as depicted in FIG. 4.

EXAMPLE 2

Preparation of Ceftiofur Sodium Crystalline (Anhydrous) Buffered Using Form A

Anhydrous crystalline sterile Ceftiofur sodium (140 g) was blended with lyophilized mixture of potassium dihydrogen orthophosphate and sodium hydroxide (4.04 g; prepared according to the process provided in 2023/CHE/2007) till to get uniform pH. HPLC purity: 99.82%
Advantages:
Enhanced stability even at elevated temperature.
High purity and non-hygroscopic in nature.
Good Colour, flow-properties and high bulk density.
Suitable dissolubility & improved shelf life.

EXAMPLE 3

Preparation of Crystalline Ceftiofur Sodium Having Moisture Content 3.0-4.5% (Form M)

The crystalline Ceftiofur sodium having moisture content about 9.0-10% (prepared according to the process provided in WO 2007/042917) was heated under vacuum at 70° C. in a oven for 6-7 hours till the moisture content reaches 3.0 to 4.5% to yield the title compound having the powder XRD pattern substantially same as depicted in FIG. 2 and having TGA curve same as depicted in FIG. 5
Purity: 99.38%. Moisture content: 4.13%.

EXAMPLE 4

Crystalline sterile Ceftiofur sodium having moisture content 3-4.5% was blended with lyophilized mixture of potassium dihydrogen orthophosphate and sodium hydroxide (prepared according to the process provided in IN2023CHE2007) till to get uniform pH. HPLC purity: 99.32%

We claim:
1. Crystalline polymorph of Ceftiofur sodium of formula (I)

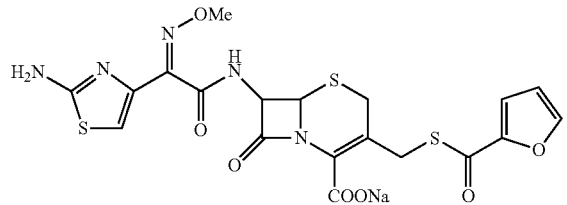

(I)

having an X-ray diffraction pattern, which comprises 2θ values (Cu K alpha–1 λ=1.5406 A° .) of 5.68, 6.54, 8.84, 12.82, 13.16, 16.33, 17.36, 18.71, 18.94, 20.25, 21.53, 22.11, 22.79, 24.44, 24.88, 25.46, and 27.00 (±0.2°2θ).

2. Crystalline polymorph of Ceftiofur sodium of formula (I) having an X-ray diffraction pattern, which comprises 2θ values (Cu K alpha–1 λ=1.5406 A° .) of 5.32, 5.47, 6.38, 8.63, 9.79, 9.99, 12.68, 14.70, 14.98, 18.73, 21.26, 22.00, 22.59, 24.29, 24.71 and 25.65 (±0.2°2θ).

3. Crystalline polymorph of Ceftiofur sodium of formula (I) as claimed in claim 1, having a same X-ray diffractogram as set out in FIG. 1.

4. Crystalline polymorph of Ceftiofur sodium of formula (I) as claimed in claim 2, having a same X-ray diffractogram as set out in FIG. 2.

5. Crystalline Ceftiofur sodium as claimed in claim 1, having a moisture content in the range of 0.4 to 2.0%.

6. Crystalline Ceftiofur sodium as claimed in claim 2, having a moisture content in the range of 3.0-4.5%.

7. A process for the preparation of the crystalline polymorph of Ceftiofur sodium of formula (I) as claimed in claim 1, which comprises drying Ceftiofur sodium (Form D) having a moisture content in the range of 7.0 to 11.0% at a temperature in the range of 60° C. to 125° C. until the moisture content reaches 0.4 to 2.0%.

8. A process as claimed in claim 7, wherein the drying is performed under vacuum or under normal pressure.

9. A process for the preparation of the crystalline polymorph of Ceftiofur sodium of formula (I) as claimed in claim 2, which comprises drying Ceftiofur sodium (Form D) having a moisture content in the range of 7.0 to 11.0% at 70° C. until the moisture content reaches 3.0 to 4.5%.

10. A process as claimed in claim 9, wherein the drying is performed under vacuum.

11. A pharmaceutical composition comprising the crystalline Ceftiofur sodium of claim 1 and a buffer.

12. Physical admixture of the crystalline Ceftiofur sodium according to claim 1, with lyophilized composition of potassium dihydrogen orthophosphate and sodium hydroxide.

13. A pharmaceutical composition comprising a mixture of crystalline Ceftiofur sodium as claimed in claim 1 with amorphous Ceftiofur sodium.

14. A pharmaceutical composition comprising the crystalline Ceftiofur sodium of claim 2 and a buffer.

15. Physical admixture of the crystalline Ceftiofur sodium according to claim 2, with lyophilized composition of potassium dihydrogen orthophosphate and sodium hydroxide.

16. A pharmaceutical composition comprising a mixture of the crystalline Ceftiofur sodium as claimed in claim 2 with amorphous Ceftiofur sodium.

* * * * *